United States Patent
Vadney

(10) Patent No.: US 11,963,734 B1
(45) Date of Patent: Apr. 23, 2024

(54) ARM SLEEVE

(71) Applicant: Mark V. Vadney, Lawton, OK (US)

(72) Inventor: Mark V. Vadney, Lawton, OK (US)

(*) Notice: Subject to any disclaimer, the term of this patent is extended or adjusted under 35 U.S.C. 154(b) by 620 days.

(21) Appl. No.: 16/826,608

(22) Filed: Mar. 23, 2020

Related U.S. Application Data

(63) Continuation of application No. 14/998,715, filed on Feb. 5, 2016, now abandoned.

(60) Provisional application No. 62/285,990, filed on Nov. 16, 2015.

(51) Int. Cl.
  *A61B 46/27* (2016.01)
  *A61B 46/00* (2016.01)
  *A61B 46/20* (2016.01)

(52) U.S. Cl.
  CPC .............. *A61B 46/27* (2016.02); *A61B 46/40* (2016.02); *A61B 2046/201* (2016.02)

(58) Field of Classification Search
  CPC ......... A61B 46/27; A61B 46/20; A61B 46/00; A61B 46/10; A61B 2046/201; A61B 46/40; A61B 46/17; A61B 46/13; A61B 2046/205; A61B 46/23; A61B 2046/234; A61B 2046/236; A61B 46/30; A41D 13/08; A41D 13/1245; A41D 27/10; A41D 13/055; A41D 13/0556; A41D 13/0562; A61F 5/37; A61F 5/3723; A61F 5/3761; A61F 13/041; A61F 15/004
  USPC ...... 128/856, 877, 849, 846, 852, 855; 2/16, 2/270, 59, 125, 126, 128; 602/3
  See application file for complete search history.

(56) References Cited

U.S. PATENT DOCUMENTS

| | | | |
|---|---|---|---|
| 1,183,225 A | 5/1916 | Overmeyer | |
| 2,693,794 A | 11/1954 | Neville | |
| 3,196,870 A | 7/1965 | Sprecher et al. | |
| 3,640,273 A | 2/1972 | Ray | |
| 3,824,998 A | 7/1974 | Snyder | |
| 3,934,582 A * | 1/1976 | Gorrie | A61B 46/27 602/62 |
| 3,989,040 A * | 11/1976 | Lofgren | A61B 46/27 128/856 |
| 4,036,220 A | 7/1977 | Bellasalma | |
| 4,253,451 A | 3/1981 | Solomon | |

(Continued)

OTHER PUBLICATIONS

USPTO, U.S. Appl. No. 14/998,715, Vadney, Office Action dated Apr. 27, 2018, 41 pages.

(Continued)

*Primary Examiner* — Victoria Hicks Fisher
(74) *Attorney, Agent, or Firm* — Dunlap Codding, P.C.

(57) ABSTRACT

An operating table arm board arm sleeve is disclosed, comprising a first rectangular flexible material having left and right edges extending substantially parallel to a longitudinal axis of the arm board between proximal and distal ends of a top side of the arm sleeve; and a bottom side comprising a second rectangular flexible material having left and right edges extending substantially parallel to the longitudinal axis between proximal and distal ends of the bottom side of the arm sleeve, the bottom side having a length and width equal to the length and width of the top side, the bottom side distal end attached to the top side distal end and cooperating to form a closed distal end, the left edge of the bottom side fastenable to the left edge of the top side, and the right edge of the bottom side fastenable to the right edge of the top side.

16 Claims, 2 Drawing Sheets

(56) References Cited

U.S. PATENT DOCUMENTS

| | | | |
|---|---|---|---|
| 4,286,588 A | | 9/1981 | Lovegrove |
| 4,308,864 A | | 1/1982 | Small et al. |
| 4,375,809 A | | 3/1983 | Meals |
| 4,945,925 A | | 8/1990 | Garcia |
| 5,291,903 A | | 3/1994 | Reeves |
| 5,845,643 A | * | 12/1998 | Vergano .............. A61F 5/05866 128/877 |
| 8,079,365 B2 | * | 12/2011 | Block .................... A61B 46/00 128/853 |
| 2008/0296193 A1 | * | 12/2008 | Haskin ................ B65D 75/002 383/42 |
| 2011/0125112 A1 | | 5/2011 | Bainbridge |
| 2013/0167845 A1 | | 7/2013 | Grajek et al. |
| 2013/0211425 A1 | * | 8/2013 | Parsell .................... A61M 1/92 606/131 |
| 2014/0150805 A1 | * | 6/2014 | Berdia ................... A61B 46/40 128/849 |

OTHER PUBLICATIONS

USPTO, U.S. Appl. No. 14/998,715, Vadney, Response to Office Action dated Apr. 27, 2018, 51 pages.
USPTO, U.S. Appl. No. 14/998,715, Vadney, Final Office Action dated Dec. 21, 2018, 25 pages.
USPTO, U.S. Appl. No. 14/998,715, Vadney, Response to Final Office Action dated Dec. 21, 2018, 12 pages.

* cited by examiner

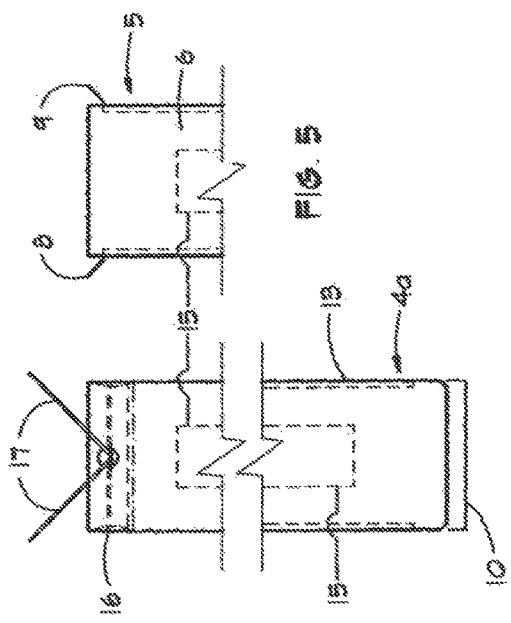
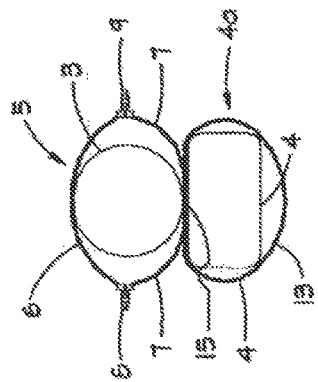
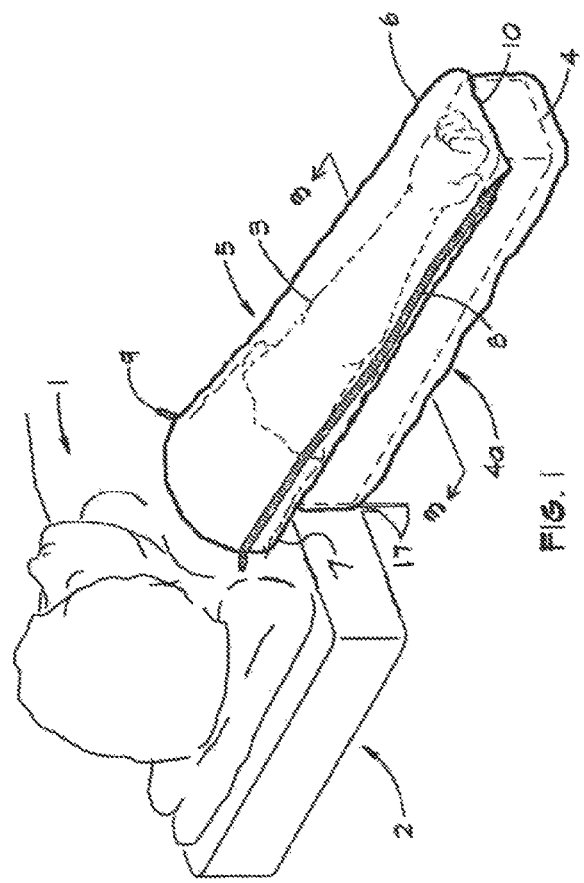
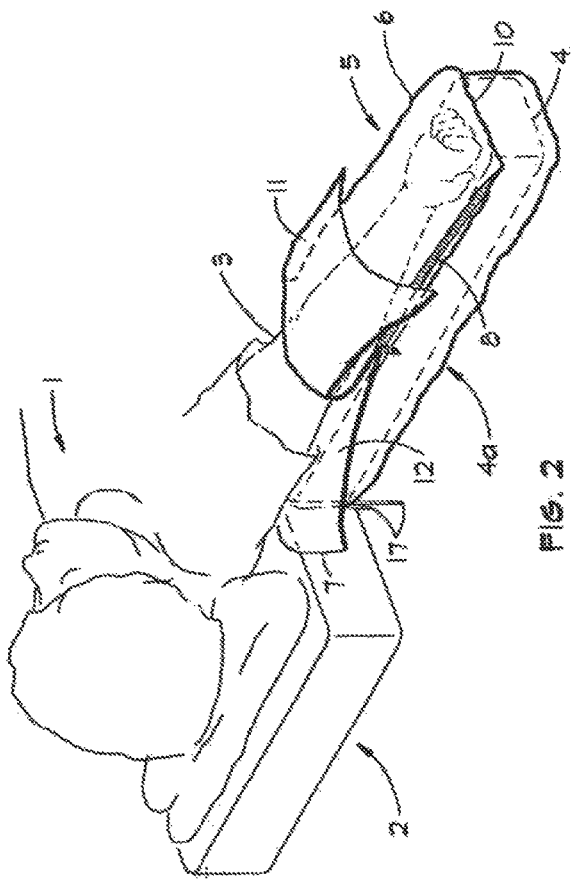

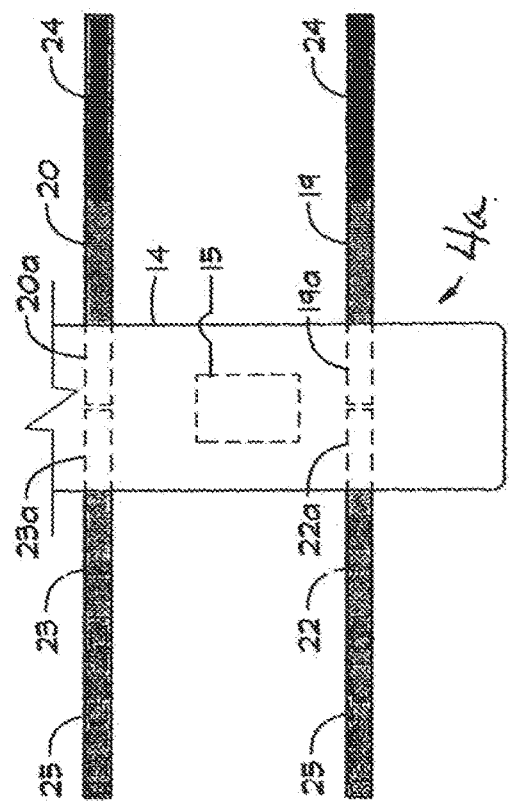
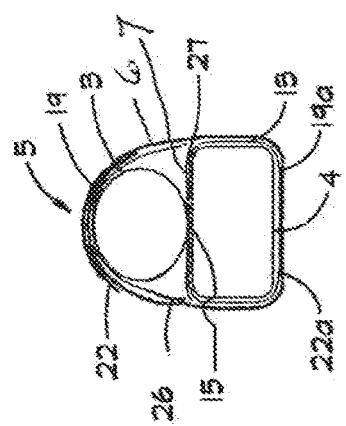
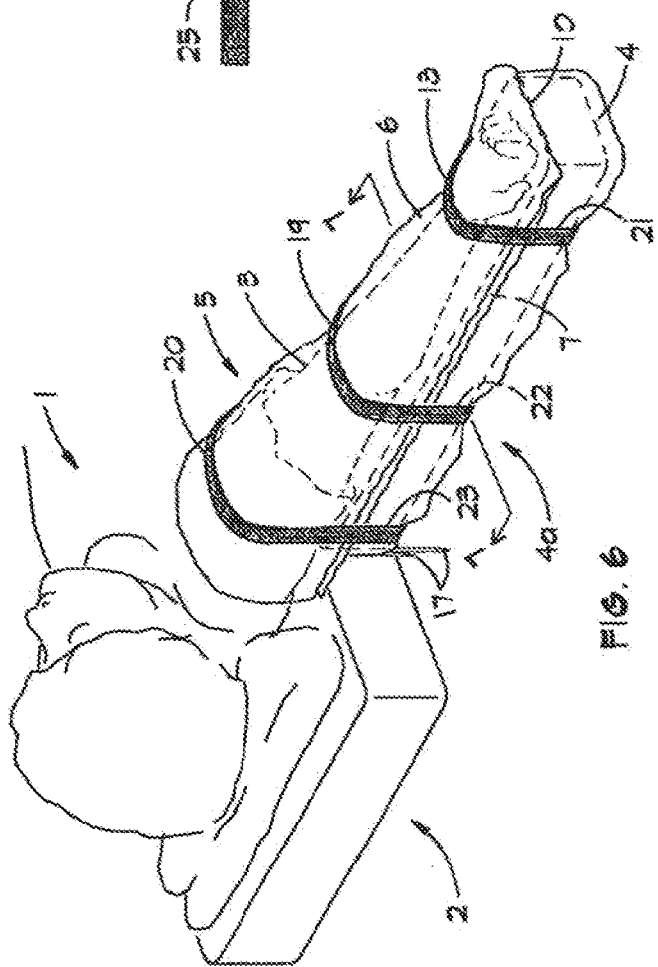

ARM SLEEVE

CROSS-REFERENCE TO RELATED APPLICATIONS

This application is a continuation of and claims priority to U.S. patent application Ser. No. 14/998,715, filed Feb. 5, 2016, entitled "Arm Sleeve", which is a non-provisional application of and claims priority to provisional application 62/285,990, filed Nov. 16, 2015, the entire contents of each of which are hereby incorporated herein by reference.

BACKGROUND OF THE INVENTION

Technical Field of the Invention

This invention relates to surgical procedures. It more particularly relates to equipment, fixtures and auxiliary items employed by medical personnel during the performance of a surgical procedure. This invention specifically relates to an article of manufacture employed to protect equipment, fixtures and personnel involved in the performance of a surgical procedure.

A surgical procedure can, and usually does, require a patient, upon whom a surgical procedure is being performed, to lie face-up on a horizontal surface, such as an operating table. Medical personnel actively engaged in the performance of the surgical procedure are positioned around the edges of the operating table. The medical personnel require convenient and ready access to the patient to enable the performance of tasks necessarily required in the performance of the procedure.

Description of the Prior Art and Problems Solved

During performance of a surgical procedure, it can be, and usually is, necessary that an arm of the patient on the operating table be positioned to enable ready and convenient access to the arm. This is accomplished by placing and supporting the arm on a flat, rigid board having a transverse axis and a longitudinal axis, wherein the longitudinal axis of the board is substantially perpendicular to the longitudinal axis of the operating table. The arm is positioned palm up on the top side of the board which is longer and wider than the arm. The board is referred to in the art as an arm board.

A task involved in a surgical procedure is the intermittent, as well as the continuous, introduction of various liquids, hereinafter referred to as medical liquids, into the patient during the performance of the surgical procedure. It is known that introduction of a medical liquid can be accomplished by causing the medical liquid to flow into the patient through a blood vessel of the patient's arm which is supported by an arm board. This task involves exposing and positioning the arm away from the immediate locale of the surgery in order to avoid, or at least to minimize, interference with medical personnel actively engaged in other tasks involved in the surgical procedure. With the arm positioned and exposed, a needle is inserted into a blood vessel and a medical liquid from a separate source is permitted to flow through a tube to the needle and then into the blood vessel.

The patient's arm which is to receive the flowing medical liquid is extended away from the operating table and placed on an arm board in an anatomical neutral position to prevent injury. Such a position, in practice, is palm up with the arm board fixed at an angle which is substantially perpendicular to the operating table, and substantially at the same level as the patient lying on the table. An arm can remain unsecured to the arm board. However, restraining straps can be, and usually are, employed to immobilize and secure the arm to the arm board. The arm board can be an integral part of the operating table or it can be a separate free-standing fixture.

While an arm is immobilized on an arm board, the arm and arm board are subject to being contacted by various liquids necessarily involved in or resulting from the surgical procedure. Such liquids include bodily liquids, such as blood and sweat, tissue discharged or removed from the patient and spillage of medical liquids. Bodily liquids, tissue and medical liquids are a source of contamination for the patient, medical personnel and exposed equipment and fixtures, including the arm board.

Arm board contamination is addressed by Reeves in U.S. Pat. No. 5,291,903. Reeves discloses a hollow, cylindrical and flexible material, which he refers to as a flexible sheath, to cover and contain the arm board. The flexible sheath has a closed end, an open end, a top side and a bottom side. The arm board is inserted into the flexible sheath which completely covers the top side of the arm board and substantially completely covers the bottom side of the arm board. The open end of the flexible sheath is positioned adjacent the operating table and the closed end is positioned at the end of the arm board away from the operating table. The flexible sheath is longer than the arm board. Accordingly, when the arm board is positioned in the interior of the flexible sheath it is completely enclosed within the flexible sheath. The Reeves flexible sheath prevents direct contact between contaminates and the arm board. Reeves discloses that straps are employed to secure the exposed arm of the patient to the arm board which is enclosed in the flexible sheath.

The Reeves flexible sheath can consist of two layers of materials, one layer of which is an inner liquid impermeable layer and the second layer of which is an outer liquid absorbent layer. The inner impermeable layer directly contacts the arm board and prevents liquid and tissue contact with the arm board. The outer absorbent layer directly contacts the extended arm and absorbs liquids and traps tissue. Liquids are absorbed by the outer absorbent layer of the flexible sheath, but the arm board is protected by the inner liquid impermeable layer of the flexible sheath. The inner impermeable layer can be integrally connected to the outer absorbent layer.

Reeves does not disclose or suggest any means for protection of the arm secured to the arm board.

SUMMARY OF THE INVENTION

This invention provides an article of manufacture and a method of using the article to prevent contact between an arm board and bodily fluids, medical fluids and tissue which are generated, produced and/or spilled during the performance of a surgical procedure. The article can also include means for securing and immobilizing a patient's arm which is supported on the arm board. In use, the article of this invention secures the arm of a patient to an arm board, prevents contamination of the arm board by bodily and medical liquids and tissue, protects the arm of a patient from environmental hazards, such as cool temperatures, normally associated with an operating room, and permits access to the arm of a patient during the performance of a surgical procedure. The article is disposable, to thereby ease the task of cleaning the arm board at the conclusion of a surgical procedure.

The article, in one aspect, is an arm sleeve. The article, in another aspect, is a combination of a separate arm sleeve and a separate arm board cover. The article, in still another aspect, is an arm sleeve attached to an arm board cover. Restraint straps (also referred to as restraining straps) can be employed in combination with each of the mentioned aspects to help prevent movement of the arm during performance of the surgical procedure and to help secure the arm to the arm board.

The article of this invention enables immobilization of the arm on the arm board, and shields the arm board from the mentioned sources of contamination. The article of this invention also enables introduction of liquids into and withdrawal of liquids from the arm, inspection of tissue during performance of the procedure and protection of the arm.

In one aspect, the article of this invention is an elongated, hollow sleeve which completely encloses and isolates the arm of a surgical patient, wherein the arm in the sleeve is supported by an arm board during the performance of a surgical procedure. The sleeve is referred to herein as an arm sleeve. The arm sleeve extends from the edge of the operating table to a point beyond the length of the extended arm. The purpose of the arm sleeve is to prevent contact of the arm board by bodily and medical liquids and tissue which are generated, produced and/or spilled during the performance of a surgical procedure. The sleeve by itself can, at least, partially limit movement of the arm in the sleeve, but the arm in the sleeve is preferably secured to the arm board by restraining straps to prevent movement of the arm and to retain the arm on the arm board.

In another aspect, the article of this invention includes an arm sleeve in combination with an arm board cover. In this aspect, the arm sleeve and arm board cover are independent items and are not attached. The arm board cover enhances the protection provided by the arm sleeve to still further prevent contact of the arm board by bodily and medical liquids and tissue which are generated, produced and/or spilled during the performance of a surgical procedure. As previously stated, the arm sleeve by itself can, at least partially, limit movement of the arm in the sleeve, but the arm in the arm sleeve is preferably secured to the arm board equipped with an arm board cover by restraining straps to prevent movement of the arm and to retain the arm on the arm board.

In still another aspect, the article of this invention is comprised of an arm sleeve physically attached to an arm board cover. In this aspect, the arm board cover enhances the protection provided by the arm sleeve as previously described. The physical attachment of the arm sleeve to the arm board cover can limit movement of the arm in the sleeve relative to the arm board, but the arm in the arm sleeve can be still further secured to the arm board by restraining straps to prevent movement of the arm and to retain the arm on the arm board.

The article of this invention can consist of the attached arm sleeve and arm board cover as previously described wherein restraining straps are physically attached to the bottom side of the arm board cover to facilitate connection of the restraining straps at points contiguous to the top side of the arm sleeve.

The arm sleeve of this invention receives, contains, isolates, encloses and aids in the immobilization of an arm of a patient lying on an operating table while the arm in the arm sleeve rests on an arm board positioned adjacent to the operating table. The arm sleeve prevents direct contact between the arm and anything which an uncovered arm might directly contact during the surgical procedure, such as the arm board, an arm board cover, bodily and medical liquids, bacteria, low temperature environments and medical personnel. The arm sleeve can be opened to expose the interior of the sleeve and to facilitate placement of the arm in the sleeve and to expose the arm in the sleeve to enable tasks directly involving the arm.

The principle purpose of the arm sleeve is to deter, if not to prevent, direct contact between an arm by any exterior surface or thing or environment which might contact an uncovered arm. Such a lack of direct contact deters contamination of both the arm and the exterior surface of anything or environment. In view of the stated purpose of the arm sleeve, the material of construction of the arm sleeve is liquid impermeable.

The arm sleeve is a hollow, flexible structure which, in one embodiment, is comprised of one rectangular flexible material transversely folded at the midpoint of the longitudinal axis of the material to form a top side and a bottom side. The top side and the bottom side are connected together along opposite longitudinal edges. The connected edges, together with the transverse fold, cooperate to form the hollow, flexible structure. The formed structure has a top side, a bottom side, an open end, a closed end (the transverse fold), a left edge, which can be independently opened and closed, and a right edge, which can be independently opened and closed. The arm sleeve may be changed between a first state and a second state, the first state in which the left edge of the bottom side has the closed connection to the left edge of the top side and the right edge of the bottom side is fastened to the right edge of the top side, such that the arm sleeve receives an arm of a patient that is resting on the arm board while the body of the patient is lying on the operating table, the second state in which the left edge of the bottom side has the closed connection and the right edge of the bottom side is partially or fully open from the right edge of the top side, such that the arm sleeve allows access to at least a portion of the arm of the patient. The open end of the structure is substantially circular in cross section. In another embodiment, the arm sleeve can be comprised of two rectangular flexible materials having equal longitudinal and transverse dimensions. The two rectangular flexible materials are connected together at one end to form the closed end of the hollow, flexible structure.

The flexible material employed in the arm sleeve is at least liquid impermeable. The material can consist of a single impermeable layer and a single absorbent layer or it can be a single layered material. The rectangular flexible material(s), when positioned in the produced hollow and flexible structure, is(are) arranged so that the liquid impermeable surfaces of the material are the outer surfaces of the sleeve and the liquid absorbent surfaces of the material are the inner surfaces of the sleeve.

The arm board cover is an elongated, hollow and flexible cylinder having a top side, a bottom side, a closed first end and an open second end. The open end is located adjacent to the operating table (the proximal end) and includes means to close and secure the proximal end of the cover against the arm board enclosed in the cover.

The purpose of the arm board cover is to protect the arm board from the sources of contamination, referred to above, which are exterior to the arm board. In this connection, the material of construction of the arm board cover can have the same mechanical and chemical properties as the material employed in the arm sleeve, but the arm board cover preferably consists of an inner liquid impermeable layer and an outer liquid absorbent layer.

DESCRIPTION OF THE DRAWINGS

FIG. 1 depicts a surgical patient lying face up on an operating table. The right arm of the patient is shown perpendicularly extended from the edge of the table and resting palm up on an arm board. The arm board is enclosed in an arm board cover. The arm is enclosed in an arm sleeve. The edges of the arm sleeve are shown to be connected by a zip fastener. FIG. 1 does not show straps encircling the arm board and arm.

FIG. 2 is modified version of FIG. 1 in which the fastened edges of the arm sleeve are shown to be partially open to illustrate the patient's arm enclosed within the arm sleeve.

FIG. 3 is a cross sectional view of FIG. 1 taken in the direction of the patient lying on the operating table. The view shows the arm board enclosed in the arm board cover, the patient's arm enclosed in the arm sleeve and the edges of the arm sleeve connected by zip fasteners.

FIG. 4 is a bottom view of FIG. 1 taken in the vertically upward direction showing the proximal end of the closed arm board cover. The view also shows, in dotted lines, the location and connection of the bottom side of the arm sleeve to the top side of the arm board cover.

FIG. 5 is a partial top view of FIG. 1 showing the closed connection of the left and right edges of the arm sleeve at the proximal end of the arm sleeve. This view also partially shows, in dotted lines, the location and connection of the bottom side of the arm sleeve to the top side of the arm board cover.

FIG. 6 shows a surgical patient lying face up on an operating table. The right arm of the patient is shown perpendicularly extended from the edge of the table and resting palm up on an arm board. The arm board is enclosed in an arm board cover. The arm is enclosed in an arm sleeve. The edges of the arm sleeve are connected by hook and loop fasteners. The view also shows restraining straps encircling the arm board cover, the arm board, the arm sleeve and the arm. The ends of the restraining straps are connected by a hook and loop fasteners at locations contiguous to the top side of the arm sleeve.

FIG. 7 is a cross sectional view of FIG. 6 taken through a strap in the direction of the patient lying on the operating table. The view shows the arm board enclosed in the arm board cover, the patient's arm enclosed in the arm sleeve, the edges of the arm sleeve connected by hook and loop fasteners and the ends of the strap connected by a hook and loop fastener.

FIG. 8 is a partial top view of FIG. 6 taken in the downward direction showing the arm board cover in which restraining straps extend perpendicular to the longitudinal axis of the arm board cover. The arm sleeve is intentionally not shown in FIG. 8. Segments of the restraining straps are shown in dotted lines connected to the bottom side of the arm board cover. The view also shows, in dotted lines, the location and connection of the bottom side of the arm sleeve to the top side of the arm board cover.

DESCRIPTION OF THE INVENTION

FIGS. 1 and 2 are partial views of patient 1 lying face up on operating table 2. Right arm 3 is extended substantially perpendicular to patient 1 and rests, palm up, on arm board 4, which is enclosed in arm board cover 4a. FIG. 1 shows right arm 3 to be fully enclosed in arm sleeve 5. Accordingly, FIG. 1 shows arm 3 and arm board 4 in dotted lines. FIG. 2 shows arm 3 to be partially exposed and partially covered. FIGS. 1 and 2 illustrate that arm sleeve 5 can be partially opened and partially closed to enable the performance of tasks associated with arm 3 during a surgical procedure. FIG. 2 shows arm board 4 in dotted lines.

As shown in FIGS. 1, 2 and 3, arm sleeve 5 has a top side 6 and a bottom side 7. Sides 6 and 7 have longitudinal side edges which are substantially parallel to the longitudinal axis of arm board 4 which is substantially perpendicular to operating table 2. The left edges of sides 6 and 7 are opened and closed by any suitable means, such as zip fastener 8 or a hook and loop fastener (not shown). Similarly, the right edges of top side 6 and bottom side 7 can be opened and closed by any suitable means, such as zip fastener 9 or a hook and loop fastener (not shown). Edge fasteners, such as zip fasteners 8 and 9, can be independently and separately, partially or completely, opened and closed to either entirely or partially expose arm 3. The closed (distal) end 10 of arm sleeve 5, in one embodiment, is formed by a transverse fold at the midpoint of the longitudinal axis of a single rectangular flexible material. The fold, therefore, operates to form top side 6, bottom side 7 and the left and right edges of arm sleeve 5. A result of the transverse fold is to identify inner surface 11 of top side 6 and inner surface 12 of bottom side 7. Inner surfaces 11 and 12 directly contact arm 3 which is enclosed in arm sleeve 5.

The combination of closed distal end 10 and sides 6 and 7, when closed by zip fasteners 8 and 9, produce arm sleeve 5 which takes the form of a tapered, hollow and flexible structure having a top side, a bottom side, a closed end and an open end. Arm 3 is positioned on inner surface 12 of arm sleeve 5 before sides 6 and 7 are closed. Necessary tasks can be performed on uncovered arm 3 before sides 6 and 7 are closed by use of fasteners 8 and 9. During the surgical procedure either one or both of fasteners 8 and 9 can be independently opened and closed to inspect the arm and perform further tasks on exposed arm 3.

Top side 6 and bottom side 7 can be two separate rectangular flexible materials of equal length and width which are attached at closed distal end 10, by any means, such as by sewing, gluing or heating. With that single exception, the above description of arm sleeve 5 is not changed.

The purpose of arm sleeve 5 is to deter, if not to prevent, direct contamination of any surface or thing or environment which might contact an uncovered arm. Arm sleeve 5, accordingly, prevents direct contact between bodily and medical liquids and tissue on arm 3 with anything which an uncovered arm might directly contact during the surgical procedure.

Similarly, the purpose of sleeve 5 is also to deter, if not to prevent, direct contamination of a covered arm which might contact any exterior surface or thing or environment. Arm sleeve 5, accordingly, prevents direct contact between body and medical liquids and tissue with anything which an uncovered arm might directly contact during the surgical procedure.

Examples of items which arm sleeve 5 seeks to protect include the arm board, medical personnel and equipment and the arm itself against extraneous liquids, bacteria, low temperature environments and medical personnel.

FIGS. 3 and 4 show bottom side 13 of arm board cover 4a and distal end 10 of arm sleeve 5. In an embodiment of the invention, bottom side 7 of arm sleeve 5 is attached to top side 14 of arm board cover 4a. Dotted line 15 shows the boundaries of the connection of bottom side 7 of sleeve 5 and top side 14 of arm board cover 4a. Arm 3, when enclosed in sleeve 5, is still further immobilized due to the connection of arm sleeve 5 to arm board cover 4a which is itself restrained by arm board 4.

The connection between bottom side 7 of sleeve 5 and top side 14 of cover 4a can be accomplished by any means known in the art such as by sewing, gluing or heating.

As seen in FIG. 4, proximal end 16 of arm board cover 4a includes a set of draw strings 17 which are enclosed in a pouch formed in end 16 of cover 4a. Tension in strings 17 is increased by pulling the strings through the pouch. Strings 17 are then tied on the underside of arm board cover 4a to thereby close arm board cover 4a against arm board 4.

FIG. 5 shows the closed connection produced by fasteners 8 and 9 of the left and right edges of sides 6 and 7 at the proximal end of arm sleeve 5. Side 7 is not shown because FIG. 5 is a top view of FIG. 1. FIG. 5 also partially shows, by dotted line 15, the location and connection of bottom side 7 of arm sleeve 5 to top side 14 of arm board cover 4a.

The flexible material employed in arm sleeve 5 must be able to substantially trap and maintain bodily liquids, medical liquids and tissue within the interior of sleeve 5, and it must be able to substantially prevent the transfer of exterior liquids and tissue into the interior of sleeve 5. The material must, therefore, be flexible; it must have adequate tensile strength and tear resistance. The flexible material can be any material having adequate tensile strength and tear resistance. The material is preferably liquid impermeable and, more preferably, both liquid absorbent and liquid impermeable. In one preferred embodiment, the outer surfaces of arm sleeve 5, to maintain bodily liquids, medical liquids and tissue within the interior of sleeve 5, are liquid impermeable. Inner surface 11 of top side 6 and inner surface 12 of bottom side 7 can be either liquid impermeable or liquid absorbent.

In one embodiment, this invention is a combination of an arm sleeve and an arm board cover, wherein the flexible material employed in the arm sleeve is as described in the preceding paragraph. However, arm board cover 4a functions to prevent the transfer of exterior liquids and tissue into the interior of arm board cover 4a. In a broad sense, the flexible material employed in arm board cover 4a need only be liquid impermeable. However, the inner surface of arm board cover 4a must be liquid impermeable and the outer surface can be liquid impermeable or liquid absorbent.

The flexible material employed in arm sleeve 5 can be a combination of two separate materials wherein one is liquid impermeable and one is liquid absorbent. In another aspect, the flexible material can be a laminate consisting essentially of a liquid impermeable layer and a liquid absorbent layer.

An example of a laminate useful as the flexible material employed in arm sleeve 5 is made of polypropylene fibers. The material is a trilaminate construction, more specifically identified as an SMS (meltblown, spunbound, meltblown) nonwoven fabric consisting of three layers: a meltblown layer, a spunblown layer and a meltblown layer. Surgical gowns are made from an SMS nonwoven fabric.

The flexible materials used in arm board cover 4a and arm sleeve 5 can be the same.

The descriptions of elements identified in FIGS. 1, 2, 3, 4 and 5 by reference numerals 1, 2, 3, 4, 4a, 5, 6, 7, 10, 14 and 17 are identical to the elements identified by reference numerals 1, 2, 3, 4, 4a, 5, 6, 7, 10, 14 and 17 in FIGS. 6, 7, and 8.

Restraining straps 18 and 21, 19 and 22, and 20 and 23 are shown in FIG. 6 positioned around arm board cover 4a, arm board 4, arm 3 and arm sleeve 5. Straps 18 and 21, 19 and 22 and 20 and 23 are connected together by hook and loop fasteners above and contiguous to arm sleeve 5.

FIG. 7 is a section showing restraining straps 19 and 22 connected together above and contiguous to arm sleeve 5. FIGS. 7 and 8 show segment 19a of strap 19 connected to bottom side 13 of arm board cover 4a. FIGS. 7 and 8 also show segment 22a of strap 22 connected to bottom side 13 of arm board cover 4a. Segments 20a and 23a of restraining straps 20 and 23 are similarly connected.

As shown in FIGS. 6 and 8, restraining straps 18, 19, and 20 are equipped with hook portions 24 and restraining straps 21, 22, and 23 are equipped with loop portions 25. As shown in FIG. 7 the loop portion of a restraining strap is placed under the hook portion of a restraining strap to produce a hook and loop connection. As shown in FIG. 8, the respective hook and loop portions are on opposite sides of connecting restraining straps in order to effect the connection shown in FIG. 7.

Top side 6 and bottom side 7 are opened and closed by hook and loop fasteners 26 and 27. The edges of sides 6 and 7 can be overlapped to produce the hook and loop connections.

What is claimed is:

1. A method, comprising:
   securing an arm sleeve to an arm board of an operating table, the operating table having a longitudinal axis, the arm board comprising a flat, rigid board having a longitudinal axis substantially perpendicular to the longitudinal axis of the operating table, the arm sleeve comprising:
   a top side comprising a first rectangular flexible material having a proximal end, a distal end, a left edge, and a right edge, the left edge and the right edge of the top side extending substantially parallel to the longitudinal axis of the arm board between the proximal end and the distal end of the top side of the arm sleeve, the top side having a first length and a first width; and
   a bottom side comprising a second rectangular flexible material having a proximal end, a distal end, a left edge, and a right edge, the left edge and the right edge of the bottom side extending substantially parallel to the longitudinal axis of the arm board between the proximal end and the distal end of the bottom side of the arm sleeve, the left edge of the bottom side having a closed connection to the left edge of the top side, and the right edge of the bottom side fastenable to the right edge of the top side and openable; and
   changing the arm sleeve between a first state and a second state, the first state in which the left edge of the bottom side has the closed connection to the left edge of the top side and the right edge of the bottom side is fastened to the right edge of the top side, such that the arm sleeve receives an arm of a patient that is resting on the arm board while the body of the patient is lying on the operating table, the second state in which the left edge of the bottom side has the closed connection and the right edge of the bottom side is partially or fully open from the right edge of the top side, such that the arm sleeve allows access to at least a portion of the arm of the patient that is resting on the arm board while the body of the patient is lying on the operating table.

2. The method of claim 1, wherein the arm sleeve comprises a zip fastener or a hook and loop fastener, and wherein the left edge of the bottom side is fastenable to the left edge of the top side with the zip fastener or the hook and loop fastener.

3. The method of claim 1, wherein the arm sleeve comprises a zip fastener or a hook and loop fastener, and wherein the right edge of the bottom side is fastenable to the right edge of the top side with the zip fastener or the hook and loop fastener.

4. The method of claim 1, wherein the top side and the bottom side of the arm sleeve each have an inner surface and an outer surface, and wherein the outer surfaces of the top side and the bottom side of the arm sleeve are liquid impermeable.

5. The method of claim 4, wherein the inner surfaces of the top side and the bottom side of the arm sleeve are liquid absorbent.

6. The method of claim 4, wherein the inner surfaces of the top side and the bottom side of the arm sleeve are liquid impermeable.

7. The method of claim 1, wherein the first rectangular flexible material of the top side and the second rectangular flexible material of the bottom side of the arm sleeve have a trilaminate construction.

8. The method of claim 1, wherein the first rectangular flexible material of the top side and the second rectangular flexible material of the bottom side of the arm sleeve are nonwoven fabric consisting of a first meltblown layer, a spunblown layer, and a second meltblown layer.

9. A method, comprising:
securing an arm sleeve and arm board cover combination to an arm board of an operating table, the operating table having a longitudinal axis, the arm board comprising a flat, rigid board having a longitudinal axis substantially perpendicular to the longitudinal axis of the operating table, the arm sleeve and arm board cover combination comprising:
an arm sleeve, comprising:
a top side comprising a first rectangular flexible material having a proximal end, a distal end, a left edge, and a right edge, the left edge and the right edge of the top side extending substantially parallel to the longitudinal axis of the arm board between the proximal end and the distal end of the top side of the arm sleeve, the top side having a first length and a first width; and
a bottom side comprising a second rectangular flexible material having a proximal end, a distal end, a left edge, and a right edge, the left edge and the right edge of the bottom side extending substantially parallel to the longitudinal axis of the arm board between the proximal end and the distal end of the bottom side of the arm sleeve, the left edge of the bottom side having a closed connection to the left edge of the top side, and the right edge of the bottom side fastenable to the right edge of the top side and openable; and
an arm board cover enclosing the arm board, the arm board cover having a top side, a bottom side, a first end, and a second end cooperating to form a hollow and flexible cylinder, wherein the first end of the arm board cover is closed and the second end of said arm board cover is open to enclose the arm board, wherein the top side of the arm board cover is attached to the bottom side of the arm sleeve; and
changing the arm sleeve between a first state and a second state, the first state in which the left edge of the bottom side has the closed connection to the left edge of the top side and the right edge of the bottom side is fastened to the right edge of the top side, such that the arm sleeve receives an arm of a patient that is resting on the arm board while the body of the patient is lying on the operating table, the second state in which the left edge of the bottom side has the closed connection and the right edge of the bottom side is partially or fully open from the right edge of the top side, such that the arm sleeve allows access to at least a portion of the arm of the patient that is resting on the arm board while the body of the patient is lying on the operating table.

10. The method of claim 9, wherein the arm sleeve further comprises a zip fastener or a hook and loop fastener, and wherein the left edge of the bottom side of the arm sleeve is fastenable to the left edge of the top side of the arm sleeve with the zip fastener or the hook and loop fastener.

11. The method of claim 9, wherein the arm sleeve further comprises a zip fastener or a hook and loop fastener, and wherein the right edge of the bottom side of the arm sleeve is fastenable to the right edge of the top side of the arm sleeve with the zip fastener or the hook and loop fastener.

12. The method of claim 9, wherein the first rectangular flexible material of the top side of the arm sleeve and the second rectangular flexible material of the bottom side of the arm sleeve each have an inner liquid-absorbent layer and an outer liquid-impermeable layer, and wherein the arm board cover comprises a second flexible material having an inner liquid-impermeable layer and an outer liquid-absorbent layer.

13. The method of claim 9, wherein the first rectangular flexible material of the top side of the arm sleeve and the second rectangular flexible material of the bottom side of the arm sleeve have a trilaminate construction.

14. The method of claim 9, wherein the first rectangular flexible material of the top side of the arm sleeve and the second rectangular flexible material of the bottom side of the arm sleeve are nonwoven fabric consisting of a first meltblown layer, a spunblown layer, and a second meltblown layer.

15. The method of claim 9, wherein the arm board cover comprises a flexible material having a trilaminate construction.

16. The method of claim 9, wherein the arm board cover comprises nonwoven fabric consisting of a first meltblown layer, a spunblown layer, and a second meltblown layer.

* * * * *